US00PP12050P2

(12) United States Plant Patent
Zary

(10) Patent No.: US PP12,050 P2
(45) Date of Patent: Aug. 14, 2001

(54) MINIATURE ROSE PLANT NAMED 'JACBUNCH'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/400,369

(22) Filed: Sep. 21, 1999

(51) Int. Cl.[7] ..... A01H 5/00
(52) U.S. Cl. ..... Plt./128
(58) Field of Search ..... Plt./128, 129, 121, Plt./122

*Primary Examiner*—Howard J. Locker
(74) *Attorney, Agent, or Firm*—Klarquist Sparkman Campbell Leigh & Whinston, LLP

(57) ABSTRACT

A miniature rose plant having compact, upright, well branched growth habit; small, bright, deep pink flowers of high centered form presented in large clusters; and small, dark green, glossy, disease resistant foliage.

1 Drawing Sheet

1

The present invention relates to a new and distinct variety of rose plant of the miniature class which was originated by me by crossing the variety 'JACient', (U.S. Plant Pat. No. 6,725), with an unnamed seedling (not patented).

The primary objective of this breeding was to produce a new rose variety having the vigor and health of the female parent as well as its high centered flowers, coupled with the very dwarf habit, small foliage and profuse flowering of the unnamed male parent. Flower color was expected to be pink, as both parents are in the pink flower range. The objected was substantially achieved, along with other desirable improvements, as evidenced by the following unique combination of characteristics that are outstanding in the new variety and that distinguish it from its parents, as well as from all other varieties of which I am aware:

1. Compact, upright, well branched habit of growth;
2. Small flowers of high centered form presented in large clusters;
3. Small, dark green, glossy foliage;
4. Good resistance to disease; and
5. Bright, deep pink flowers.

Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACient' (U.S. Plant Pat. No. 6,725).

*Pollen parent.*—Unnamed seedling (not patented).

Classification:

*Botanical.*—*Rosa hybrida.*

*Commercial.*—Miniature.

2

FLOWER

Observations made from specimens grown in a garden environment at Somis, Calif. from February 1998 to August 1999.

Blooming habit: Continuous.

Bud:

*Size.*—¾ inch long when the petals start to unfurl.

*Form.*—The bud form is long, pointed ovoid.

*Color.*—When sepals first divide, the bud color is Red Group 46C. When half blown, the upper and lower sides of the petals are Red Group 47D.

*Sepals.*—Color: Green Group 138B, except when exposed to bright sunlight, then the sepals become Greyed-Purple Group 187A. Surface texture: Covered in fine hairs. There are three lightly appendaged sepals. There are two unappendaged sepals with hairy edges.

*Receptacle.*—Color: Green Group 137A, except where exposed to bright sun, then the color is Greyed-Purple Group 183A. Shape: Funnel. Size: Small, about ¼ inch×3/16 inch. Surface: Smooth.

*Peduncle.*—Length: Short, about 1½ inches. Surface: Smooth, with an occasional gland. Color: Green Group 137A with Greyed-Purple Group 183A where the peduncle has been exposed to bright sun. Strength: Stiff, erect.

Bloom:

*Size.*—Small. Average open diameter is about 2½ inches.

*Borne.*—Singly and several together, in rounded clusters of three to seven blooms.

*Stems.*—Strength: Strong. Average length is about six to eight inches.

*Form.*—When first open: High centered. Permanence: Flattens; all petals curl.

*Petalage.*—Number of petals under normal conditions: 35.

*Color.*—The upper sides of the petals are Red Group 47D. The reverse sides of the petals are Red Group 47D. The base of each petal has a small, 3/16 inch×3/16 inch, Yellow-Orange Group 15D half moon at the point of attachment on the upper surface. The lower surface has a similar half moon, but it is only ⅛ inch×⅛ inch. The major color on the upper sides is Red Group 47D.

*Variegations.*—There is an occasional greenish-white streak on the guard petals.

*Discoloration.*—The general tonality at the end of the first day: No change. At the end of the third day: A change from Red Group 46C in the opening bud to Red Group 47D in the open flower.

*Fragrance.*—Slight.

Petals:

*Texture.*—Thick.

*Shape.*—Deltoid.

*Form.*—Tips slightly recurved.

*Arrangement.*—Imbricated. There are no petaloids in the center.

*Persistence.*—Petals drop off cleanly before drying.

*Lastingness.*—On the plant: Fair (about 4–5 days). As a cut flower: Fair (about 6 days).

Reproductive parts:

*Anthers.*—Size: Medium. Quantity: Many. Color: Yellow-Orange Group 18B. Arrangement: Regular around styles.

*Filaments.*—Color: Yellow Group 4C.

*Pollen.*—Present.

*Styles.*—Color: Red Group 53C.

*Stigmas.*—Color: Yellow-White Group 158B.

Plant:

*Form.*—Bush.

*Growth.*—Vigorous, upright, branching, compact. At maturity, height is 30 inches, width is 24 inches.

Foliage: Number of leaflets on normal mid-stem leaves: Five.

*Size.*—Small (3½ to 4 inches long×2½ to 3 inches wide).

*Quantity.*—Abundant.

*Color.*—New foliage: Upper and lower surfaces: Greyed-Red Group 178A. Old foliage: Upper surface: Green Group 136A. Lower surface: Green Group 136B.

Leaflets:

*Shape.*—Pointed oval.

*Texture.*—Leathery; glossy.

*Edge.*—Serrated.

*Serration.*—Single; small.

*Petiole rachis.*—Color: Upper: Greyed-Purple Group 183A. Lower: Green Group 137C.

*Petiole underside.*—Smooth,with occasional prickles.

*Stipules.*—Short (about ⅝ inch); serrated; bearded.

*Disease resistance.*—Resistant to mildew and rust, susceptible to blackspot under normal growing conditions.

Wood:

*New wood.*—Color: Greyed-Red Group 178A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 183A.

*Color when mature.*—Greyed-Orange Group 174D.

Small prickles:

*Quantity.*—On main stalks: None. On laterals: None.

I claim:

1. A new and distinct variety of rose plant of the miniature class, substantially as herein shown and described, characterized particularly by its compact, upright, well branched growth habit; small, bright, deep pink flowers of high centered form presented in large clusters; and small, dark green, glossy, disease resistant foliage.

* * * * *

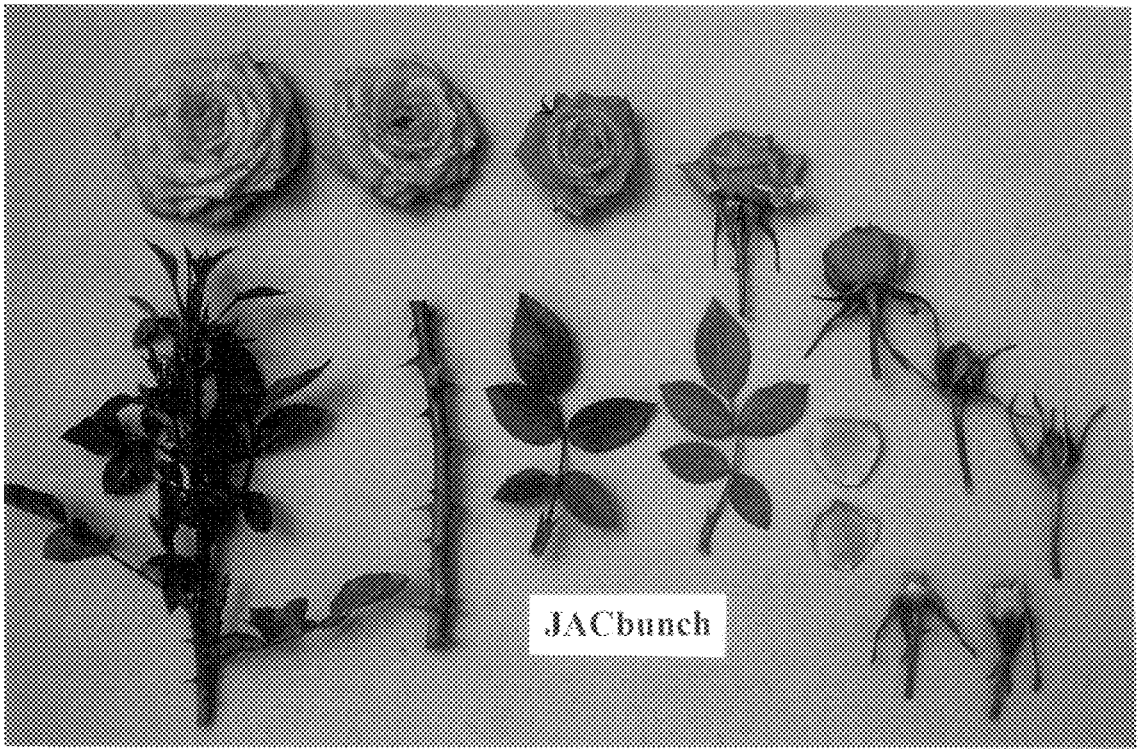
JACbunch